United States Patent
Sunagawa et al.

(10) Patent No.: US 6,265,396 B1
(45) Date of Patent: Jul. 24, 2001

(54) β-LACTAM COMPOUNDS AND PROCESS FOR PREPARING THE SAME

(75) Inventors: Makoto Sunagawa, Itami; Hiroshi Yamaga, Suita; Hiroshi Nouda, Itami; Hisatoshi Shinagawa, Takatsuki, all of (JP)

(73) Assignee: Sumitomo Pharmaceuticals Co., Ltd., Osaka-fu (JP)

( * ) Notice: Subject to any disclaimer, the term of this patent is extended or adjusted under 35 U.S.C. 154(b) by 0 days.

(21) Appl. No.: 09/254,175

(22) PCT Filed: Sep. 3, 1997

(86) PCT No.: PCT/JP97/03078
§ 371 Date: Mar. 2, 1999
§ 102(e) Date: Mar. 2, 1999

(87) PCT Pub. No.: WO98/09965
PCT Pub. Date: Mar. 12, 1998

(30) Foreign Application Priority Data

Sep. 4, 1996 (JP) .................................. 8-255450

(51) Int. Cl.[7] ...................... C07D 477/20; A61K 31/407; A61P 31/04
(52) U.S. Cl. ...................................... 514/210.12; 540/350
(58) Field of Search ...................... 514/210.12; 540/350

(56) References Cited

U.S. PATENT DOCUMENTS

| | | |
|---|---|---|
| 4,477,662 | 10/1984 | Corbett et al. ........................ 544/212 |
| 4,840,946 | 6/1989 | Habich et al. ........................ 514/210 |
| 5,104,867 | 4/1992 | Kawamoto et al. ................... 514/210 |
| 5,153,187 | 10/1992 | Iwasaki et al. ....................... 514/210 |
| 5,519,015 | 5/1996 | Jung ................................ 514/210.13 |
| 5,750,686 | 5/1998 | Sunagawa et al. ................... 540/350 |

FOREIGN PATENT DOCUMENTS

| | | |
|---|---|---|
| 0010317 | 4/1980 | (EP) . |
| 0017992 | 10/1980 | (EP) . |
| 0061231 | 9/1982 | (EP) . |
| 0071908 | 2/1983 | (EP) . |
| 0160876 | 11/1985 | (EP) . |
| 61-5081 | 1/1986 | (JP) . |
| 63-63680 | 3/1988 | (JP) . |
| 7-2856 | 1/1995 | (JP) . |
| 94-29313 | 12/1994 | (WO) . |
| WO9604282 | 2/1996 | (WO) . |

OTHER PUBLICATIONS

Sumita et al., "Antimicrobial Activity of SM–17466, a Novel Carbapenem Antibiotic with Potent Activity against Methicillin–Resistant *Staphylococcus aureus*", Antimicrobial Agents and Chemotherapy, Apr. 1995, pp. 910–916.

Sunagawa et al., "Synthesis and biological properties of a new series of anti–MRSA beta–lactams; 2–(thiazol–2'–ylthio) carbapenems", Bioorganic & Medicinal Chemistry Letters, vol. 4, No. 23, pp. 2793–2798 (1994).

*Primary Examiner*—Mark L. Berch
*Assistant Examiner*—Thomas C. McKenzie
(74) *Attorney, Agent, or Firm*—Birch, Stewart, Kolasch and Birch, LLP

(57) ABSTRACT

A β-lactam compound of the formula:

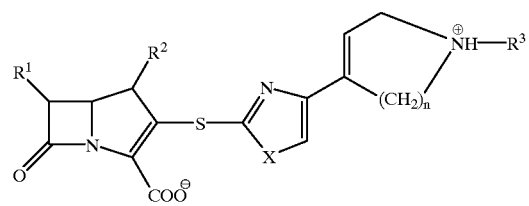

[1]

wherein $R^1$ is lower alkyl or OH-substituted lower alkyl, $R^2$ is H or lower alkyl, X is O, S or NH, n is 1 to 3, $R^3$ is —$C(R^a)$=NH ($R^a$ is H, lower alkyl or substituted lower alkyl), or a salt thereof, or an ester thereof. These compounds show excellent antibacterial activity against Gram-positive bacteria, particularly against methicillin-resistant Staphylococci and methicillin-resistant and coagulase-negative Staphylococci.

7 Claims, No Drawings

β-LACTAM COMPOUNDS AND PROCESS FOR PREPARING THE SAME

This application is the national phase under 35 U.S.C. §371 of PCT International Application No. PCT/JP97/03078 which has an International filing date of Sep. 3, 1997 which designated the United States of America.

TECHNICAL FIELD

The present invention relates to a novel β-lactam compound represented by the formula [1] as described below.

BACKGROUND ART

By the wide clinical application of the third-generation cephalosporins, Gram-positive bacteria have become to be frequently isolated. Particularly, methicillin-resistant *Staphylococcus aureus* (hereinafter, referred to as MRSA) has been more frequently isolated, and becomes a serious problem in clinical field, because infectious diseases caused by MRSA are difficult to be treated. For example, vancomycin, which has been broadly used for infectious diseases caused by MRSA in these days, is difficult to be administered because of its side effects, and glycopeptide-resistant bacteria are supposed to increase in future by administration thereof. Moreover, it has recently been reported the increase in isolation of methicillin-resistant and coagulase-negative Staphylococci (MRCNS). Under these circumstances, it has been desired to develop a safe drug having potent anti-MRSA and anti-MRCNS activities.

DISCLOSURE OF INVENTION

An object of the present invention is to provide a β-lactam antibiotic having an excellent antibacterial activity against Gram-positive bacteria, especially against MRSA and MRCNS.

The present inventors have intensively studied, and have found that a compound of the following formula [1] shows a potent effect on Gram-positive bacteria, and shows an excellent antibacterial activity especially against MRSA and MRCNS, and have accomplished the present invention.

That is, the present invention relates to a compound of the formula [1]:

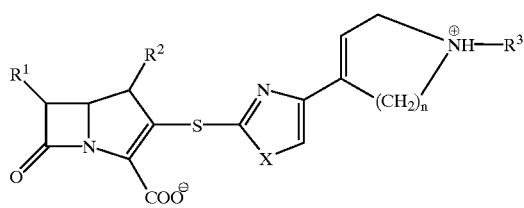

[1]

wherein $R^1$ is a lower alkyl group or a lower alkyl group being substituted by a hydroxy group, $R^2$ is a hydrogen atom or a lower alkyl group, X is O, S or NH, n is 1 to 3, and $R^3$ is —C($R^a$)=NH, in which $R^a$ is a hydrogen atom, a lower alkyl group, or a substituted lower alkyl group, or a pharmaceutically acceptable salt thereof, or a non-toxic ester thereof.

Moreover, the present invention also relates to a process for preparing a compound of the formula [1]:

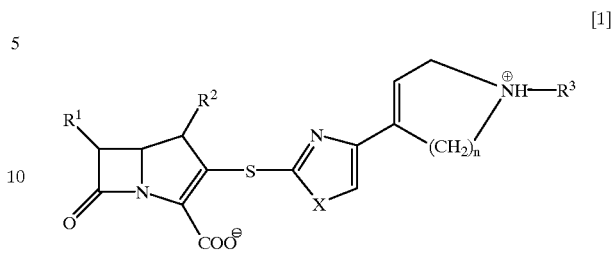

[1]

wherein $R^1$, $R^2$, $R^3{}_1$, X and n are the same as defined above, or a pharmaceutically acceptable salt thereof, or a non-toxic ester thereof, which comprises
reacting a compound of the formula [2]:

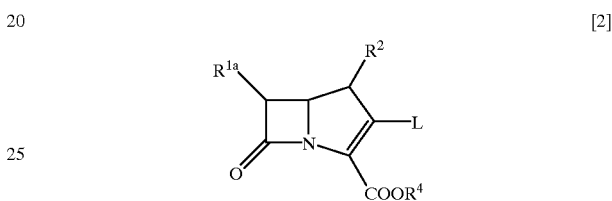

[2]

wherein $R^2$ is the same as defined above, $R^{1a}$ is a lower alkyl group, a lower alkyl group being substituted by a hydroxy group, or a lower alkyl group being substituted by a hydroxy group protected by a protecting group, $R^4$ is a protecting group for carboxyl group, and L is an active ester of hydroxy group, with a compound of the formula [3]:

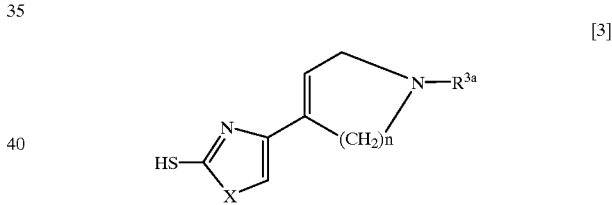

[3]

wherein X and n are the same as defined above, $R^{3a}$ is —C($R^a$)=NRb, in which $R^a$ is the same as defined above, and Rb is a hydrogen atom or a protecting group for imidoyl group, or $R^{3a}$ is a protecting group for amino group, in the presence of a base, or reacting the compound of the formula [2] with a thiolate salt of the compound of the formula [3] to give a compound of the formula [4]:

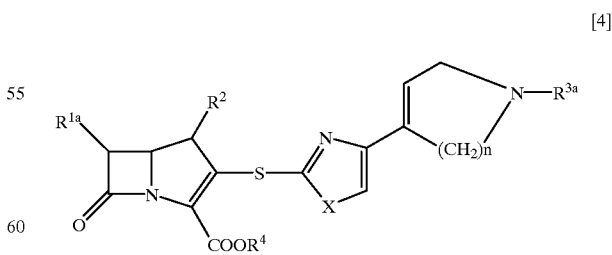

[4]

wherein $R^{1a}$, $R^2$, $R^{3a}$, $R^4$, X and n are the same as defined above,
followed by reactions which are properly selected from the removal of the protecting group for hydroxy group for $R^{1a}$, the removal of the protecting group for amino group for $R^{3a}$ and the subsequent imidoylization reaction of the de-protected amino group, or the removal of the protecting group for imidoyl group for $R^{3a}$, and the removal of the protecting group for carboxyl group for $R^4$.

The lower alkyl group for $R^1$, $R^{1a}$, $R^2$, $R^3$ or $R^{3a}$ in the above formulae [1], [2], [3] and [4] includes alkyl groups having 1 to 5 carbon atoms, for example, methyl, ethyl, n-propyl, isopropyl, n-butyl, isobutyl, tert-butyl, and n-pentyl.

The lower alkyl group being substituted by a hydroxy group for $R^1$ or $R^{1a}$ includes alkyl groups having 1 to 5 carbon atoms and being substituted by a hydroxy group, for example, hydroxymethyl, 1-hydroxyethyl, 2-hydroxyethyl, 1-hydroxy-1-methylethyl, 1-hydroxypropyl, and 2-hydroxypropyl.

The substituent for the substituted lower alkyl group in the present invention includes, for example, a hydroxy group; a lower alkoxy group; a lower alkoxy group being substituted by a hydroxy group or an amino group; a lower alkylcarbonyloxy group; a lower alkoxycarbonyl group; an amino group; an amino group being substituted by one or two group selected from a lower alkyl group and a lower alkyl group being substituted by a hydroxy group or an amino group; a guanidino group; a quaternary ammonium group being substituted by three groups selected from a lower alkyl group and a lower alkyl group being substituted by a hydroxy group or an amino group; a carboxyl group; an aminocarbonyl group; an aminocarbonyl group being substituted by one or two groups selected from a lower alkyl group and a lower alkyl group being substituted by a hydroxy group or an amino group; a halogen atom; a cyano group; an alkylamidino group having 1 to 3 carbon atoms; and a guanidinocarbonyl group. These substituents may optionally be protected by an appropriate protecting group. The positions of these substituents may be any position which is chemically possible, and the substitution either at one position or at more positions such as 1 to 3 positions is also available. The substituted lower alkyl group also includes ones forming a 3- to 7-membered ring via a heteroatom that is a substituent. The 3- to 7-membered ring thus formed includes rings such as aziridine, azetidine, pyrrolidine, piperidine, morpholine, homopiperazine, and tetrahydrofuran.

The protecting group for carboxyl group for $R^4$ in the above formulae [2] and [4] may be any conventional protecting groups, but preferably a straight chain or branched chain lower alkyl group having 1 to 5 carbon atoms (e.g., methyl, ethyl, isopropyl, tert-butyl, etc.), a halogeno-lower alkyl group having 1 to 5 carbon atoms (e.g., 2-iodoethyl, 2,2,2-trichloroethyl), a lower alkoxymethyl group having 1 to 5 carbon atoms (e.g., methoxymethyl, ethoxymethyl, isobutoxymethyl), a lower aliphatic acyloxymethyl group having 2 to 5 carbon atoms (e.g., acetoxymethyl, propionyloxymethyl, butyryloxymethyl, pivaloyloxymethyl), a 1-($C_1$–$C_5$)alkoxycarbonyloxyethyl group (e.g., 1-ethoxycarbonyloxyethyl), an aralkyl group (e.g., benzyl, p-methoxybenzyl, o-nitrobenzyl, p-nitrobenzyl), a lower alkenyl group having 3 to 7 carbon atoms (e.g., allyl, 3-methylallyl), a benzhydryl group, or a phthalidyl group.

The protecting group for hydroxy group for $R^{1a}$ in the formulae [2] and [4], and the protecting group for imidoyl group and the protecting group for amino group for $R^{3a}$ in the formulae [3] and [4] may be any conventional ones, but preferably an alkoxycarbonyl group having 1 to 5 carbon atoms (e.g., tert-butyloxycarbonyl), a halogenoalkoxycarbonyl group having 1 to 5 carbon atoms (e.g., 2-iodoethyloxycarbonyl, 2,2,2-trichloroethyloxycarbonyl), a substituted or unsubstituted alkenyloxycarbonyl group having 3 to 7 carbon atoms (e.g., allyloxycarbonyl), an aralkyloxycarbonyl group (e.g., benzyloxycarbonyl, p-methoxybenzyloxycarbonyl, o-nitrobenzyloxycarbonyl, p-nitrobenzyloxycarbonyl), or a trialkylsilyl group (e.g., trimethylsilyl, triethylsilyl, tert-butyldimethylsilyl).

The pharmaceutically acceptable salt of the compound of the above formula [1] is a conventional non-toxic salt thereof. Such salts include, as a salt with an intramolecular carboxylic acid, a salt with an inorganic base such as sodium, potassium, calcium, magnesium, ammonium, a salt with an organic base such as triethylammonium, pyridinium, diisopropylammonium, or an intramolecular salt being formed with a cation at the 3-side chain such as a quaternary ammonium ion. As a salt with an intramolecular base, a salt with an inorganic acid such as hydrochloric acid, sulfuric acid, phosphoric acid, or a salt with an organic acid such as formic acid, acetic acid, oxalic acid, methanesulfonic acid, benzenesulfonic acid can be exemplified.

The non-toxic ester of the compound [1] includes a conventional pharmaceutically acceptable ester at the 2-carboxyl group of carbapenem antibacterial agents, and may be esters being able to be easily hydrolyzed in the living body, for example, esters with acetoxymethyl, pivaloyloxymethyl, 1-(ethoxycarbonyloxy)ethyl, and phthalidyl.

The β-lactam compound of the formula [1], a pharmaceutically acceptable salt thereof, or a non-toxic ester thereof may be in the form of an anhydride thereof, a hydrate thereof, or a solvate thereof.

The process for preparing the present compound is illustrated in more detail below.

The compound of the formula [4]:

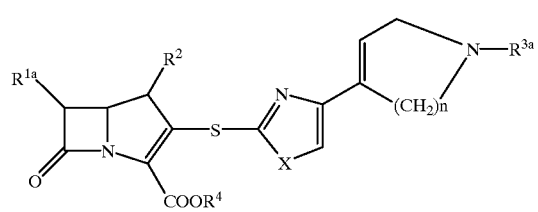

[4]

where in $R^{1a}$, $R^2$, $R^{3a}$, $R^4$, X and n are the same as defined above, can be prepared by reacting a reactive ester of the formula [2]:

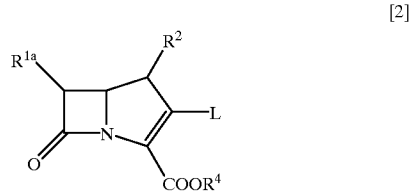

[2]

wherein $R^{1a}$, $R^2$, $R^4$ and L are the same as defined above, with a mercaptan compound of the formula [3]:

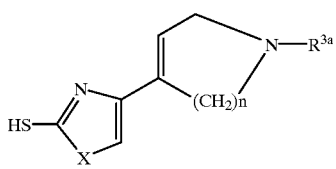

wherein $R^{3a}$, X and n are the same as defined above, in the presence of a base in an inert solvent, or by reacting a compound of the formula [2] with a thiolate salt of the compound of the formula [3] in an inert solvent.

The active ester of hydroxy group includes, for example, a substituted or unsubstituted arylsulfonic acid ester (e.g., benzenesulfonic acid ester, p-toluenesulfonic acid ester, p-nitrobenzenesulfonic acid ester, p-bromobenzenesulfonic acid ester, etc.), an alkanesulfonic acid ester having 1 to 5 carbon atoms (e.g., methanesulfonic acid ester, ethanesulfonic acid ester, etc.), a halogenoalkanesulfonic acid ester having 1 to 5 carbon atoms (e.g., trifluoromethanesulfonic acid ester, etc.), an arylphosphoric acid ester (e.g., diphenylphosphoric acid ester, etc.), or a halide compound such as chloride, bromide, iodide which is an ester with a hydrogen halide. The preferable reactive ester of hydroxy group may be p-toluenesulfonic acid ester, methanesulfonic acid ester, trifluoromethanesulfonic acid ester, and diphenylphosphoric acid ester.

The inert solvent, which is used in the reaction between the compound [2] and the compound [3] in the presence of a base to give the compound [4], includes, for example, dioxane, tetrahydrofuran, dimethylsulfoxide, dimethylformamide, acetonitrile, benzene, toluene, hexamethylphophoramide, or a mixture of these solvents.

The base includes, for example, an inorganic base such as sodium carbonate, potassium carbonate, sodium hydride, potassium hydride, or an organic base such as pyridine, dimethylaminopyridine, triethylamine, diisopropylethylamine, 1,8-diazabicyclo[5.4.0]undec-7-ene (DBU). Especially preferable one is DBU. The base should be used in an amount sufficient for carrying out the reaction, and it is usually used in an amount of 1 to 3 equivalents, to the amount of the mercaptan compound [3].

The mercaptan compound [3] should be used in an amount sufficient for carrying out the reaction, and can be used in a large excess amount, but it is usually used in an amount of 1 to 2 equivalents, to the amount of the compound [2].

The reaction is carried out at a temperature from −78° C. to +60° C., preferably at a temperature from −40° C. to +40° C. Besides, after the reaction is completely over, the product thus obtained is isolated by a conventional organic chemical method.

The inert solvent, which is used in the reaction between the compound [2] and a thiolate salt of the compound [3] to give the compound [4], includes, for example, dioxane, tetrahydrofuran, dimethylsulfoxide, dimethylformamide, acetonitrile, benzene, toluene, hexamethylphosphoramide, or a mixture of these solvents.

The thiolate salt should be used in an amount sufficient for carrying out the reaction, and can be used in a large excess amount, but it is usually used in an amount of 1 to 2 equivalents, to the amount of the compound [2].

The reaction is carried out at a temperature from −78° C. to +60° C., more preferably at a temperature from −40° C. to +40° C. After the reaction is completely over, the product thus obtained is isolated by a conventional organic chemical method.

The thiolate salt is prepared from the mercaptan compound [3] and a base. The base includes, for example, an inorganic base (e.g., sodium hydride, potassium hydride), a metal alkoxide (e.g., potassium tert-butoxide, sodium methoxide), or a metal amide (e.g., sodium amide, lithium diisopropylamide, lithium disirazide).

The β-lactam compound of the formula [1] is obtained from the compound [4] in a conventional manner, if necessary, by reactions which are properly selected from the removal of the protecting group for hydroxy group for $R^{1a}$, the removal of the protecting group for amino group for $R^{3a}$ and the subsequent imidoylization reaction of the de-protected amino group, or the removal of the protecting group for imidoyl group for $R^{3a}$, and the removal of the protecting group for carboxyl group for $R^4$.

The removal of a protecting group for hydroxy group for $R^{1a}$, the removal of a protecting group for imidoyl group for $R^{3a}$, the removal of a protecting group for amino group for $R^{3a}$, and the removal of a protecting group for carboxyl group for $R^4$ are carried out by treating with an acid, a base, or a reducing agent, and these methods per se are well known methods, as disclosed, for example, in T. W. Greene: Protective Groups in Organic Synthesis, J. Wiley & Sons Inc., 1981. The acid is preferably trifluoroacetic acid, formic acid, boron trifluoride, aluminum chloride, etc., or a mixture of these acids. The base is preferably an alkali metal carbonate (e.g., sodium carbonate, potassium carbonate, etc.), an alkali metal sulfide (e.g., sodium sulfide, potassium sulfide, etc.), or tetrabutylammonium fluoride. The reduction method includes, for example, hydrogenation with zinc and acetic acid, hydrogen and palladium-carbon or platinum, etc. The reduction is also carried out by using a combination of reducing agents such as palladium (0) or palladium (II) and tri-n-butyltin hydride.

The solvent may be any ones which do not disadvantageously affect the reaction, and includes, for example, water, alcohols (e.g., methanol, ethanol), ethers (e.g., tetrahydrofuran, dioxane), fatty acids (e.g., acetic acid), or a mixture of these solvents. The reaction can possibly be suppressed or promoted by properly lowering or raising the reaction temperature. The preferable reaction temperature is in the range from −30° C. to +40° C. After the reaction is completely over, the product thus obtained can be isolated by a conventional organic chemical method, for example, by neutralizing the reaction mixture, subjecting it to column chromatography on absorption resin, etc., collecting the fractions containing the desired compound, and then followed by lyophilizing the resultant.

The compound of the formula [2] is a well known compound, and is disclosed, for example, in JP-B-63-55514.

The mercaptan compound [3] can be prepared by conventional various methods, for example, by methods disclosed in literatures such as K. Hoffmann, Heterocyclic Chemistry vol. 6 (1953); J. V. Metzger, ibid., vol. 34 (1979); I. J. Turchi, ibid., vol. 45 (1986); Interscience Publishers, Inc. or A. R. Katritzky, Advances in Heterocyclic Chemistry, vol. 32 (1982), Academic Press, or by combining these methods. The mercaptan compound [3] is prepared, for example, by the following reaction scheme.

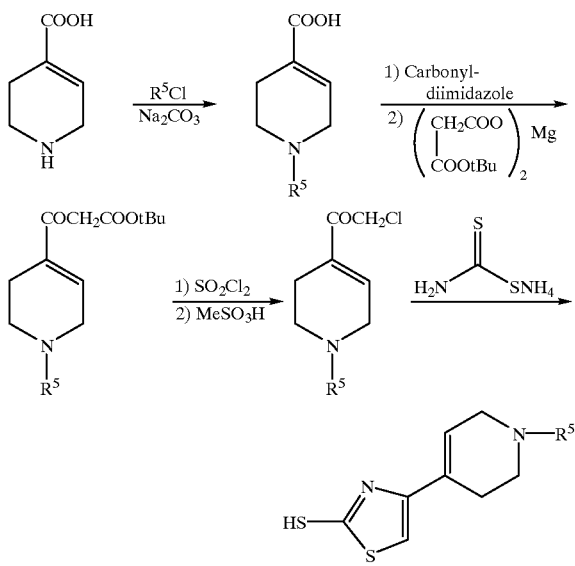

wherein $R^5$ is an imidoyl group protected by a protecting group, or a protecting group for amino group, and tBu means 1,1-dimethylethyl (tert-butyl) group. Of course, the process for preparing the mercaptan compound [3] should not be construed to be limited to the above Reaction Scheme.

The compound of the above-mentioned formula [1] may have optical isomers based on the asymmetric carbon atoms at the 4-, 5- and 6-positions of the carbapenem nucleus, as shown in the following formula:

[1]

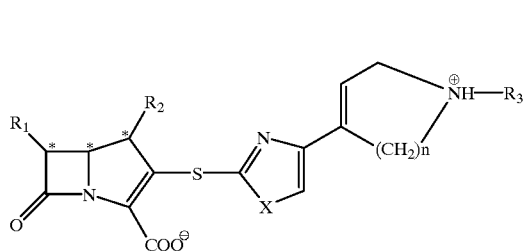

wherein $R^1$, $R^2$, $R^3$, X and n are the same as defined above, and * means an asymmetric carbon atom, and these isomers are all conveniently expressed by only one formula. However, the present invention should not be construed to be limited thereto, and includes all isomers and a mixture of isomers based on each asymmetric carbon atom. However, the preferable isomers are ones wherein when $R^2$ is a hydrogen atom, the 5-carbon atom has an R-configuration such as (5R,6R)-compounds or (5R, 6S)-compounds, and when $R^2$ is a lower alkyl group, the 4-carbon atom has an R-configuration and the 5-carbon atom has an S-configuration, such as (4R,5S,6S)-compounds or (4R,5S, 6R)-compounds. Moreover, when $R^1$ is 1-hydroxyethyl group, the compound [1] may have isomers having an R-configuration or an S-configuration at the 8-position, as shown in the following formula:

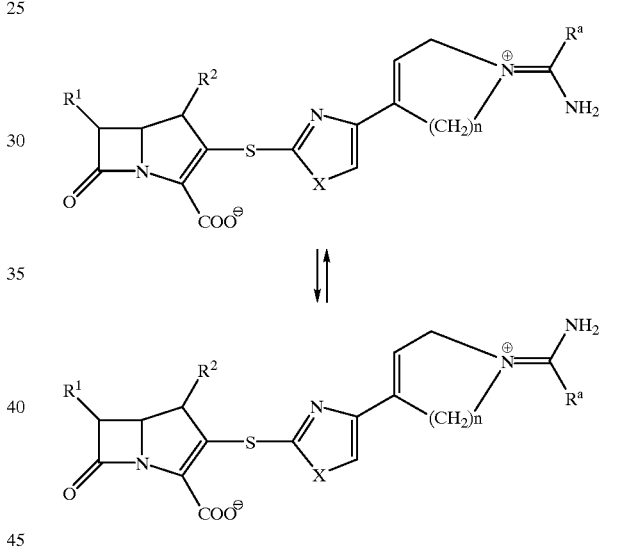

wherein $R^2$, $R^3$, X and n are the same as defined above, and the preferable one is ones having an R-configuration at the 8-position.

Isomers having such configurations are prepared by using each corresponding isomer of the starting compound [2].

In addition, the compound [1] is also considered to have tautomers of the following formula:

wherein $R^1$, $R^2$, $R^a$, X and n are the same as defined above, but the formula [1] is exemplified as a formula conveniently indicating all of these tautomers as well.

The present compounds of the formula [1] are novel β-lactam compounds having an azolethio group at the 3-position of the carbapenem nucleus, and a cycloalkenyl group at the 4-position of said azole group, and further having an amino group being substituted by various imidoyl groups within said cycloalkenyl ring. These compounds show an excellent antibacterial activity, and are useful as medicaments.

Representative compounds of the formula [1] obtained by the present invention are exemplified in the following Table 1.

TABLE 1

[1]

| Comp. No. | R¹ | R² | X | n | R³ |
|---|---|---|---|---|---|
| 1 | CH₃CH(OH)— | Me | S | 2 | —C(CH₂CH₃)=NH |
| 2 | CH₃CH(OH)— | Me | S | 2 | —C(CH₂CH₂CH₃)=NH |
| 3 | CH₃CH(OH)— | Me | S | 2 | —C(CH₂(CH₃)₂)=NH |
| 4 | CH₃CH(OH)— | Me | S | 2 | —C(CH₂OH)=NH |
| 5 | CH₃CH(OH)— | Me | S | 2 | —C(CH₂CH₂OH)=NH |
| 6 | CH₃CH(OH)— | Me | S | 2 | —C(CH₂NH₂)=NH |
| 7 | CH₃CH(OH)— | Me | S | 2 | —C(CH₂CONH₂)=NH |
| 8 | CH₃CH(OH)— | Me | S | 2 | —C(CH₂COOCH₃)=NH |
| 9 | CH₃CH(OH)— | Me | S | 2 | —C(CH₂CH₂Cl)=NH |
| 10 | HOCH₂— | Me | S | 2 | —CH=NH |
| 11 | HOCH₂— | Me | S | 2 | —C(CH₃)=NH |
| 12 | CH₃CH(OH)— | H | S | 2 | —CH=NH |
| 13 | CH₃CH(OH)— | H | S | 2 | —C(CH₃)=NH |
| 14 | CH₃CH(OH)— | Me | O | 2 | —CH=NH |
| 15 | CH₃CH(OH)— | Me | O | 2 | —C(CH₃)=NH |
| 16 | CH₃CH(OH)— | Me | NH | 2 | —CH=NH |
| 17 | CH₃CH(OH)— | Me | NH | 2 | —C(CH₃)=NH |
| 18 | CH₃CH(OH)— | Me | S | 1 | —CH=NH |
| 19 | CH₃CH(OH)— | Me | S | 1 | —C(CH₃)=NH |
| 20 | CH₃CH(OH)— | Me | S | 3 | —CH=NH |
| 21 | CH₃CH(OH)— | Me | S | 3 | —C(CH₃)=NH |

The compounds as listed in Table 1 have stereoisomers as described above, and these exemplified compounds include all of their isomers as well.

The novel β-lactam compounds represented by the above formula [1] are useful as medicaments. That is, the compounds [1] exhibit antibacterial activities against a wide variety of pathogenic bacteria including Gram-positive bacteria such as *Staphylococcus aureus, Staphylococcus epidermidis, Streptococcus pyogenes, Streptococcus pneumoniae, Enterococcus faecalis*, and Gram-negative bacteria such as *Escherichia coli*, the genus Proteus, *Klebsiella pneumoniae, Haemophilus influenzae, Neisseria gonorrhoeae*, the genus Branhamella, and especially exhibit excellent antibacterial activities against Gram-positive bacteria, as well as against MRSA and MRCNS.

It is well known that dehydropeptidase-I (DHP-I), a renal enzyme, can easily hydrolyze carbapenem compounds derived from natural resources, but some of the present compounds [1], which are also carbapenem compounds, are stable over DHP-I, and can be used alone, but a DHP-I inhibitor may be used together with the present compound, if necessary.

The present compounds have excellent physiochemical properties, for example, excellent solubility and stability in water or in an aqueous solution such as a buffer.

When used as an antibacterial agent in the treatment of infectious diseases caused by bacteria, the present compounds are administered, for example, orally in the form of a tablet, capsule, powder, syrup, etc., or parenterally such as intravenous injection, intramuscular injection, or intrarectal administration.

The suitable administration forms as mentioned above may be prepared by mixing an active ingredient with a conventional pharmaceutically acceptable carrier, excipient, binder, stabilizer, etc. When administered in the form of an injection, a pharmaceutically acceptable buffering agent, solubilizer, isotonic agent, etc. may be added thereto.

The dosage of the compound [1] varies according to the conditions, ages, weights of the patient, the administration form, the frequency of the administration, etc., but it is usually in the range of 100 to 3000 mg per day for an adult, which is administered once or divided into several dosage units. Besides, the dosage of the compound [1] may be increased or decreased, if necessary.

EXAMPLES

The present invention is illustrated in more detail by Examples, but should not be construed to be limited thereto.

The following abbreviations are used in Examples.

Ph: Phenyl group

TMS: Trimethylsilyl group

Me: Methyl group

ALOC: 2-Propenyloxycarbonyl group (Allyloxycarbonyl group)

Example 1

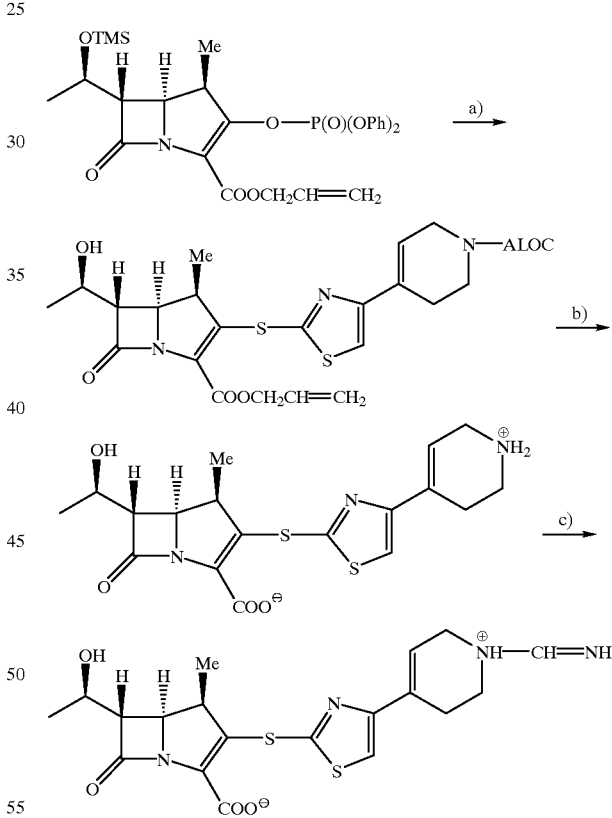

a) A solution of (4R,5R,6S,8R)-(2-propenyl)-3-(diphenylphosphoryloxy)-4-methyl-6-(1-(trimethylsilyloxy)-ethyl)-1-azabicyclo[3.2.0]hept-2-en-7-one-2-carboxylate (2.02 g, 3.53 mmol) in acetonitrile (5 ml) is stirred at 0° C., and thereto is added gradually a suspension of a thiolate salt, which is prepared by adding 2-mercapto-4-(4-(1-(2-propenyl)oxycarbonyl-1,2,5,6-tetrahydropyridyl))-thiazole (997 mg, 3.53 mmol) into a suspension of sodium hydride (101 mg, 4.23 mmol) in THF (30 ml), and the mixture is allowed to stand at 5° C. for 72 hours. The mixture is stirred at 0° C., and the pH value of the mixture is adjusted to pH 3 with iN hydrochloric acid, and the reaction mixture is stirred for 30 minutes.

The pH value of the reaction mixture is adjusted to pH 8.5 with a saturated aqueous sodium hydrogen carbonate solution, and the mixture is diluted with ethyl acetate. The organic layer is dried over magnesium sulfate, concentrated under reduced pressure, and the residue thus obtained is purified by silica gel column chromatography (solvent; hexane:ethyl acetate=10:2) to give (4R,5S,6S,8R)-(2-propenyl)-3-(4-(4-(1-(2-propenyl)oxy-carbonyl-1,2,5,6-tetrahydropyridyl))thiazol-2-ylthio)-4-methyl-6-(1-hydroxyethyl)-1-azabicyclo[3.2.0]hepto-2-en-7-one-2-carboxylate (810 mg, yield; 41%), as a pale yellow amorphous.

$^1$H-NMR δ (CDCl$_3$):1.09 (3H, d, J=6.6Hz), 1.23 (3H, d, J=7.3Hz), 2.51 (2H, brs), 3.26 (1H, m), 3.50 (1H, m), 3.69 (2H, m), 4.10 (2H, m), 4.20 (2H, m), 4.6–4.8 (4H, m), 5.0–5.5 (4H, m), 5.8–6.0 (2H, m), 6.66 (1H, s), 7.36 (1H, s)

b) (4R,5S,6S,8R)-(2-Propenyl)-3-(4-(4-(1-(2-propenyl) oxycarbonyl-1,2, 5, 6-tetrahydropyridyl) )thiazol-2-ylthio)-4-methyl-6- (1-hydroxyethyl) -1-azabicyclo [3.2.0]-hepto-2-en-7-one-2-carboxylate (610 mg, 1.09 mmol) is dissolved in m-chlorobenzene (15 g), and thereto is added aniline (2.03 g, 2.2 mmol). The mixture is stirred at room temperature under nitrogen atmosphere for 30 minutes. The reaction mixture is cooled to 0° C., and thereto is added tetrakistriphenylphosphinepalladium (62.9 mg, 0.054 mmol), and the mixture is further stirred for one hour.

To the reaction mixture are added a saturated aqueous sodium chloride solution (10 ml) and an aqueous sodium hydrogen carbonate solution (pH 8.0–8.5, 10 ml), and the mixture is washed twice with dichloromethane. The aqueous layer is concentrated under reduced pressure to remove the solvent, and the resultant is purified by polymer chromatography (CHP-20P). The fractions eluted with 4–8% aqueous THF solution are combined and lyophilized to give (4R,5S, 6S, 8R)- (3-(4-(4-(1,2,5,6-tetrahydropyridinio) )thiazol-2-yl-thio)-4-methyl-6- (1-hydroxyethyl)-1-azabicyclo[3.2.0] hepto-2-en-7-one-2-carboxylate (80 mg, yield 18%), as a white amorphous.

UV max nm (H$_2$O):313, 247 (sh)

IR max cm$^{-1}$ (KBr):3388, 1762, 1599, 1388

$^1$H-NMR δ (D$_2$O):1.10 (3H, d, J=7.3Hz), 1.27 (3H, d, J=6.6Hz), 2.83 (2H, m), 3.32 (1H, m), 3.51 (3H, m), 3.93 (2H, m), 4.26 (2H, m), 6.53 (1H, brs), 7.61 (1H, s)

c) (4R,5S,6S,8R)-(3-(4-(4-(1,2,5,6-Tetrahydropyridinio))thiazol-2-ylthio)-4-methyl-6-(1-hydroxyethyl)-1-5 azabicyclo[3.2.0]hepto-2-en-7-one-2-carboxylate (145 mg, 0.36 mmol) is dissolved in 0.1M sodium phosphate buffer (pH 7.0, 4 ml), and thereto is added at 0° C. 1N aqueous sodium hydroxide solution to adjust the pH value thereof to pH 8.5. To the mixture is added benzyl formimidate hydrochloride (389 mg, 2.88 mmol), and the pH value thereof is adjusted to pH 8.5 with iN aqueous sodium hydroxide solution, and stirred for two hours. The pH value of the reaction solution is adjusted to pH 7.0 with iN hydrochloric acid, and the mixture is washed twice with dichloromethane. The aqueous layer is concentrated under reduced pressure to remove the solvent, and the resultant is purified by polymer chromatography (CHP-20P). The fractions eluted with 4% aqueous THF solution are combined, and lyophilized to give (4R,5S,6S,8R)-3-(4-(4-(1-formimidoyl-1,2,5,6-tetrahydropyridinio))thiazol-2-ylthio)-4-methyl-6-(1-hydroxyethyl)-1-azabicyclo[3.2.0]hepto-2-en-7-one-2-carboxylate (40 mg, yield; 25%), as a white amorphous.

UV max nm (H$_2$O):314, 227

IR max cm$^{-1}$ (KBr):3401, 1764, 1710, 1596, 1384

$^1$H-NMR δ (D$_2$O):0.98 (3H, d, J=7.3Hz), 1.19 (3H, d, J=6.3Hz), 2.64 (2H, brs), 3.18–3.24 (1H, m), 3.38–3.41 (1H, m), 3.73–3.83 (2H, m), 4.13–4.19 (4H, m), 6.40 and 6.45 (totally 1H, each s), 7.45 and 7.46 (totally 1H, each s), 7.90 and 7.91 (totally 1H, each s).

Example 2

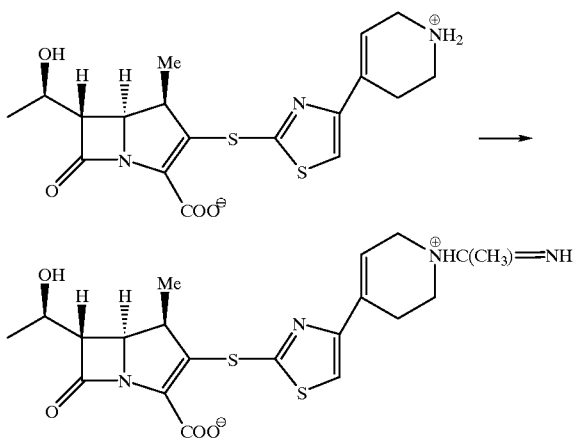

(4R,5S,6S,8R)-3-(4-(4-(1-Acetoimidoyl-1,2,5,6-tetrahydropyridinio))thiazol-2-ylthio)-4-methyl-6-(1-hydroxyethyl)-1-azabicyclo[3.2.0]hepto-2-en-7-one-2-carboxylate is obtained as a white amorphous in the same manner as in Example 1 except that ethyl acetoimidate hydrochloride is used in Step (c).

UV max nm (H$_2$O):313, 229;

IR max cm$^-$ (KBr):3354, 1762, 1603, 1381;

$^1$H-NMR δ (D$_2$O):1.05 (3H, d, J=7.3Hz), 1.25 (3H, d, J=6.3Hz), 2.37 and 2.41 (totally 3H, each s), 2.69 (2H, brs), 3.29 (1H, m), 3.47 (1H, m), 3.78–3.83 (2H, m), 4.20–4.34 (4H, m), 6.47 (1H, s), 7.53 and 7.54 (totally 1H, each s).

Reference Example

One example of a process for preparing the mercapto compound of the formula [3] is explained below. The following abbreviations are used in the following Reference Example.

Bn: Benzyl group

Et: Ethyl group

ALOC: 2-Propenyloxycarbonyl group (allyloxycarbonyl group)

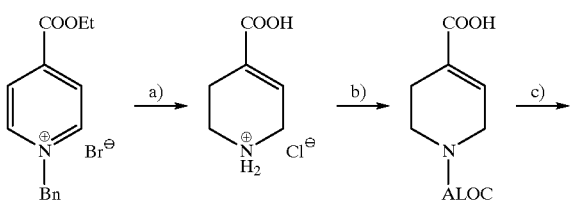

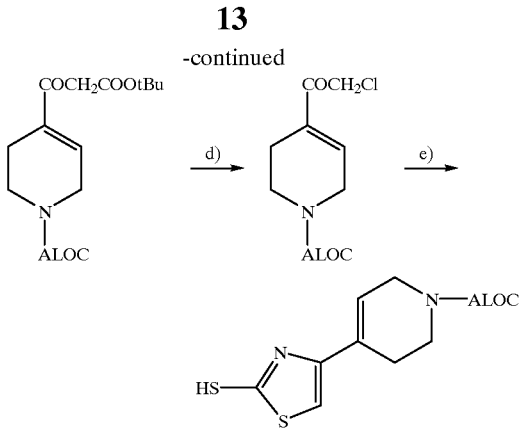

a) 1-Benzyl-4-ethoxycarbonylpyridinium bromide (580 g, 1.80 mol) is suspended in a mixture of ethanol (900 ml) and water (900 ml), and thereto is added sodium borohydride (74.9 g, 1.98 mol) in portions while the temperature of the reaction mixture is kept at a temperature below 10° C. The reaction mixture is stirred at 10° C. for three hours. The reaction mixture is concentrated under reduced pressure, and the residue is dissolved in chloroform. The mixture is washed with water, dried over sodium sulfate, and concentrated under reduced pressure to remove the solvent. The residue is dissolved in chloroform (500 ml), and thereto is added dropwise ethyl chloroformate (215 g, 1.98 mol) under reflux over a period of one hour. The mixture is further refluxed for 30 minutes, and concentrated under reduced pressure. To the residue are added conc. hydrochloric acid (504 g) and water (150 g), and the mixture is refluxed for 10 hours. The reaction mixture is cooled to room temperature, and concentrated under reduced pressure. To the residue is added isopropyl alcohol (500 ml), and the mixture is stirred. The precipitated crystals are collected by filtration with suction, and washed with a small amount of ether, and dried with air to give 1,2,5,6-tetrahydroisonicotinic acid hydrochloride (151.7 g, 52%), as white crystals.

$^1$H-NMR δ (D$_2$0):2.48 (2H, m), 3.29 (2H, m), 3.79 (2H, m), 6.81 (1H, m)

b) 1,2,5,6-Tetrahydroisonicotinic acid hydrochloride (150 g, 0.92 mol) is added to an aqueous solution of sodium carbonate (194 g, 1.83 mol) in water (920 ml), and thereto is added dropwise 2-propenyl chloroformate (116 g, 0.96 mol) under ice-cooling over a period of one hour. After the addition, the mixture is further stirred under icecooling for five hours. Separately, conc. hydrochloric acid (191 g) and dichloromethane (1000 ml) are cooled, and thereto is added dropwise the above reaction mixture in portions. The mixture is separated, and the aqueous layer is extracted twice with dichloromethane. The organic layers are combined, washed with a saturated aqueous sodium chloride solution, dried over magnesium sulfate, and concentrated under reduced pressure to remove the solvent to give 1-(2-propenyloxycarbonyl)-1,2,5,6-tetrahydro-isonicotinic acid (198.9 g, quant.) as a white solid.

$^1$H-NMR δ (CDCl$_3$):2.42 (2H, m), 3.60 (2H, m), 4.17 (2H, m), 4.63 (2H, m), 5.19–5.34 (2H, m), 5.94 (1H, m), 7.01 (1H, s), 10.47 (1H, brs)

c) 1-(2-Propenyloxycarbonyl)-1,2,5,6-tetrahydro-isonicotinic acid (114.2 g, 0.54 mol) is dissolved in THF (450 ml), and thereto is added carbonydiimidazole (105 g, 0.65 mol) at room temperature, and the mixture is stirred for 30 minutes. The mixture is added dropwise to a solution of magnesium di(mono-tert-butylmalonate) (129.6 g, 0.38 mol) in THF (800 ml) at room temperature, and then the mixture is allowed to stand overnight. The reaction mixture is diluted with ethyl acetate, and washed successively with 1N hydrochloric acid, a saturated aqueous sodium hydrogen carbonate solution, and a saturated aqueous sodium chloride solution, dried over magnesium sulfate, concentrated to remove the solvent, to give tert-butyl-4-(1-(2-propenyl)oxycarbonyl-1,2,5,6-tetrahydropyridyl)-carbonylacetate (141.4 g, 86%) as pale yellow oil.

$^1$H-NMR δ (CDCl$_3$):1.45–1.65 (9H, m), 2.41 (2H, m), 3.56–3.70 (4H, m), 4.21 (2H, m), 4.63 (2H, m), 5.20–5.35 (2H, m), 5.94 (1H, m), 6.77 (1H, s)

d) tert-Butyl-4-(1-(2-propenyl)oxycarbonyl-1,2,5,6-tetrahydropyridyl)carbonylacetate (141.1 g, 0.46 mol) is dissolved in dichloromethane (400 ml), and thereto is added tert-butanol (33.8 g, 0.46 mol). The mixture is cooled to −15 to −20° C., and thereto is added gradually dropwise sulfuryl chloride (38.8 ml, 0.48 mol) with stirring. Then, the mixture is stirred for one hour. The reaction mixture is warmed to room temperature, and thereto is added a saturated aqueous sodium hydrogen carbonate solution. The mixture is separated, and the organic layer is dried over magnesium sulfate, and concentrated to remove the solvent. The residue is dissolved in ethylene dichloride (350 ml), and thereto is added methanesulfonic acid (12.4 g, 0.13 mol). The mixture is warmed to 70° C., and stirred for four hours. The reaction mixture is cooled to room temperature, and thereto is added a saturated aqueous sodium hydrogen carbonate solution. The mixture is extracted with ethyl acetate, and the organic layer is dried over magnesium sulfate, and concentrated to remove the solvent. The residue is purified by silica gel column chromatography (hexane:ethyl acetate=10:3) to give chloromethyl-4-(1-(2-propenyl)oxycarbonyl-1,2,5,6-tetrahydropyridyl)ketone (52.9 g, 47%) as a pale yellow solid.

$^1$H-NMR δ (CDCl$_3$):2.44 (2H, m), 3.60 (2H, m), 4.27 (2H, m), 4.43 (2H, s), 4.63 (2H, m), 5.22–5.38 (2H, m), 5.95 (1H, m), 6.85 (1H, s)

e) Chloromethyl-4-(1-(2-propenyl)oxycarbonyl-1,2,5,6-tetrahydropyridyl)ketone (29.4 g, 0.12 mol) is dissolved in a mixture of ethanol (200 ml) and THF (200 ml), and thereto is added ammonium dithiocarbamate (14.2 g, 0.14 mol). The mixture is stirred at room temperature for two hours. The reaction mixture is concentrated under reduced pressure, and to the residue is added dichloromethane. The mixture is washed with water and a saturated aqueous sodium chloride solution, dried over magnesium sulfate, and concentrated to remove the solvent. The residue is dissolved in a mixture of ethanol (200 ml) and THF (200 ml), and the mixture is refluxed with stirring for two hours. The reaction mixture is cooled to room temperature, and concentrated under reduced pressure at room temperature to give 2-mercapto-4-(4-(1-(2-propenyl)oxycarbonyl-1,2,5,6-tetrahydropyridyl))thiazole (34 g, quant.).

$^1$H-NMR δ (CDCl$_3$):2.41 (2H, m), 3.68 (2H, m), 4.19 (2H, s), 4.64 (2H, m), 5.21–5.35 (2H, m), 5.95 (1H, m), 6.28 (1H, s), 6.44 (1H, s), 11.98 (1H, brs)

What is claimed is:

1. A β-lactam compound of the formula (1):

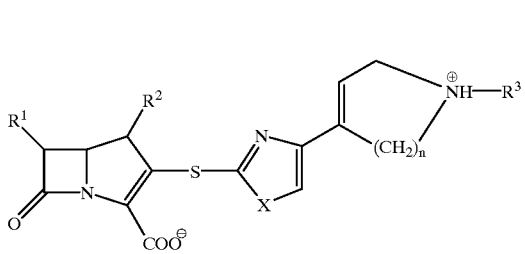

(1)

wherein $R^1$ is a lower alkyl group or a lower alkyl group being substituted by a hydroxy group, $R^2$ is a hydrogen atom or a lower alkyl group, X is O, S or NH, n is 1 to 3, and $R^3$ is —C($R^a$)=NH, in which $R^a$ is a hydrogen atom, a lower alkyl group, or a substituted lower alkyl group,
or a pharmaceutically acceptable salt thereof,
or a non-toxic ester thereof, wherein the non-toxic ester is a pharmaceutically acceptable ester at the 2-carboxyl group, selected from the group consisting of esters with acetoxymethyl, pivaloyloxymethyl, 1-(ethoxycarbonyloxy)ethyl and phthalidyl.

2. The β-lactam compound according to claim 1, wherein n is 2 or a pharmaceutically acceptable salt thereof, or a non-toxic ester thereof, wherein the non-toxic ester is a pharmaceutically acceptable ester at the 2-carboxyl group, selected from the group consisting of esters with acetoxymethyl, pivaloyloxymethyl, 1-(ethoxycarbonyloxy)ethyl and phthalidyl.

3. The β-lactam compound according to claim 2, wherein X is a sulfur atom or an oxygen atom, or a pharmaceutically acceptable salt thereof, or a non-toxic ester thereof, wherein the non-toxic ester is a pharmaceutically acceptable ester at the 2-carboxyl group, selected from the group consisting of esters with acetoxymethyl, pivaloyloxymethyl, 1-(ethoxycarbonyloxy)ethyl and phthalidyl.

4. The β-lactam compound according to claim 3, wherein $R^1$ is 1-(R)-hydroxyethyl, or a pharmaceutically acceptable salt thereof, or a non-toxic ester thereof, wherein the non-toxic ester is a pharmaceutically acceptable ester at the 2-carboxyl group, selected from the group consisting of esters with acetoxymethyl, pivaloyloxymethyl, 1-(ethoxycarbonyloxy)ethyl and phthalidyl.

5. The β-lactam compound according to claim 4, wherein X is a sulfur atom, or a pharmaceutically acceptable salt thereof, or a non-toxic ester thereof, wherein the non-toxic ester is a pharmaceutically acceptable ester at the 2-carboxyl group, selected from the group consisting of esters with acetoxymethyl, pivaloyloxymethyl, 1-(ethoxycarbonyloxy)ethyl and phthalidyl.

6. A pharmaceutical composition useful as an antibacterial agent, which comprises as an active ingredient the β-lactam compound of the formula (1) according to claim 1, 2, 3, 4, or 5, or the pharmaceutically acceptable salt thereof, or the non-toxic ester thereof, in admixture with a pharmaceutically acceptable carrier or diluent,
wherein the non-toxic ester is a pharmaceutically acceptable ester at the 2-carboxyl group, selected from the group consisting of esters with acetoxymethyl, pivaloyloxymethyl, 1-(ethoxycarbonyloxy)ethyl and phthalidyl.

7. A process for preparing a β-lactam compound of the formula (1):

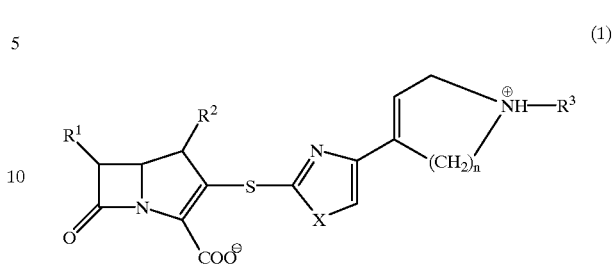

(1)

wherein $R^1$ is a lower alkyl group or a lower alkyl group being substituted by a hydroxy group, $R^2$ is a hydrogen atom or a lower alkyl group, X is O, S or NH, n is 1 to 3, and $R^3$ is —C($R^a$)=NH, in which $R^a$ is a hydrogen atom, a lower alkyl group, or a substituted lower alkyl group, or a pharmaceutically acceptable salt thereof, or a non-toxic ester thereof, wherein the non-toxic ester is a pharmaceutically acceptable ester at the 2-carboxyl group, selected from the group consisting of esters with acetoxymethyl, pivaloyloxymethyl, 1-(ethoxycarbonyloxy)ethyl and phthalidyl, which comprises reacting a compound of the formula (2):

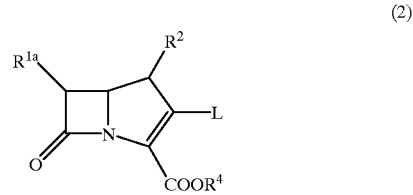

(2)

wherein $R^2$ is the same as defined above, $R^{1a}$ is a lower alkyl group, a lower alkyl group being substituted by a hydroxy group, or a lower alkyl group being substituted by a hydroxy group protected by a protecting group, $R^4$ is a protecting group for carboxyl group, and L is an active ester of hydroxy group, with a compound of the formula (3):

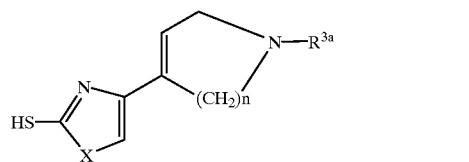

(3)

wherein X and n are the same as defined above, $R^{3a}$ is —C($R^a$)=NRb, in which $R^a$ is the same as defined above, and Rb is a hydrogen atom or a protecting group for imidoyl group, or $R^{3a}$ is a protecting group for amino group, in the presence of a base, or reacting the compound of the formula (2) with a thiolate salt of the compound of the formula (3) to give a compound of the formula (4):

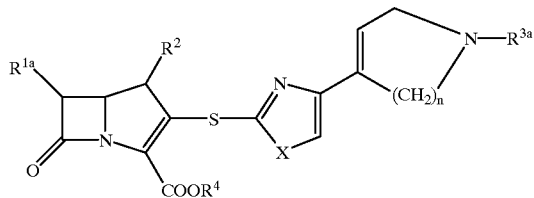

(4)

wherein $R^{1a}$, $R^2$, $R^{3a}$, $R^4$, X and n are the same as defined above, followed by reactions which are selected from the removal of the protecting group for hydroxy group for $R^{1a}$, the removal of the protecting group for amino group for $R^{3a}$ and the subsequent imidoylization reaction of the de-protected amino group, or the removal of the protecting group for imidoyl group for $R^{3a}$, and the removal of the protection group $R^4$ for carboxyl group.

* * * * *